US010416132B2

United States Patent
Chi et al.

(10) Patent No.: US 10,416,132 B2
(45) Date of Patent: Sep. 17, 2019

(54) DETECTION METHOD FOR LOW MOLECULAR WEIGHT HEPARIN COMPLETE DEGRADATION PRODUCTS USING HYDROPHILIC INTERACTION CHROMATOGRAPHY AND MULTIPLE REACTION MONITORING TANDEM MASS SPECTROMETRY

(71) Applicant: SHANDONG UNIVERSITY, Jinan (CN)

(72) Inventors: Lianli Chi, Jinan (CN); Xiaojun Sun, Jinan (CN); Anran Sheng, Jinan (CN); Xinyue Liu, Jinan (CN)

(73) Assignee: SHANDONG UNIVERSITY, Jinan (CN)

( * ) Notice: Subject to any disclaimer, the term of this patent is extended or adjusted under 35 U.S.C. 154(b) by 102 days.

(21) Appl. No.: 15/735,139

(22) PCT Filed: Feb. 27, 2017

(86) PCT No.: PCT/CN2017/074966
§ 371 (c)(1),
(2) Date: Dec. 8, 2017

(87) PCT Pub. No.: WO2017/197950
PCT Pub. Date: Nov. 23, 2017

(65) Prior Publication Data
US 2018/0149626 A1 May 31, 2018

(30) Foreign Application Priority Data
May 18, 2016 (CN) .......................... 2016 1 0330158

(51) Int. Cl.
*G01N 30/72* (2006.01)
*G01N 30/34* (2006.01)
(Continued)

(52) U.S. Cl.
CPC ......... *G01N 30/7233* (2013.01); *G01N 30/34* (2013.01); *G01N 33/6848* (2013.01);
(Continued)

(58) Field of Classification Search
CPC . G01N 30/7233; G01N 30/34; G01N 33/6848
See application file for complete search history.

(56) References Cited

PUBLICATIONS

Wang, Zhangjie et al. "Liquid chromatography-diode array detection-mass spectrometry for compositional analysis of low molecular weight heparins" Analytical Biochemistry 451 (2014) 35-41. (Year: 2014).*

* cited by examiner

*Primary Examiner* — Paul M. West
(74) *Attorney, Agent, or Firm* — CBM Patent Consulting, LLC

(57) ABSTRACT

A detection method for low molecular weight heparin complete degradation products using hydrophilic interaction chromatography and multiple reaction monitoring tandem mass spectrometry. Identifying the original reducing end and non-reducing end of enoxaparin sodium by means of reducing the reducing end of enoxaparin sodium, and performing hydrolysis using hydrogen peroxide. Performing quantitative analysis on all component units utilizing hydrophilic interaction chromatography and multiple reaction monitoring tandem mass spectrometry, in particular quantifying low-content special structures and characterizing low molecular weight heparin.

4 Claims, 3 Drawing Sheets

Figure 1:
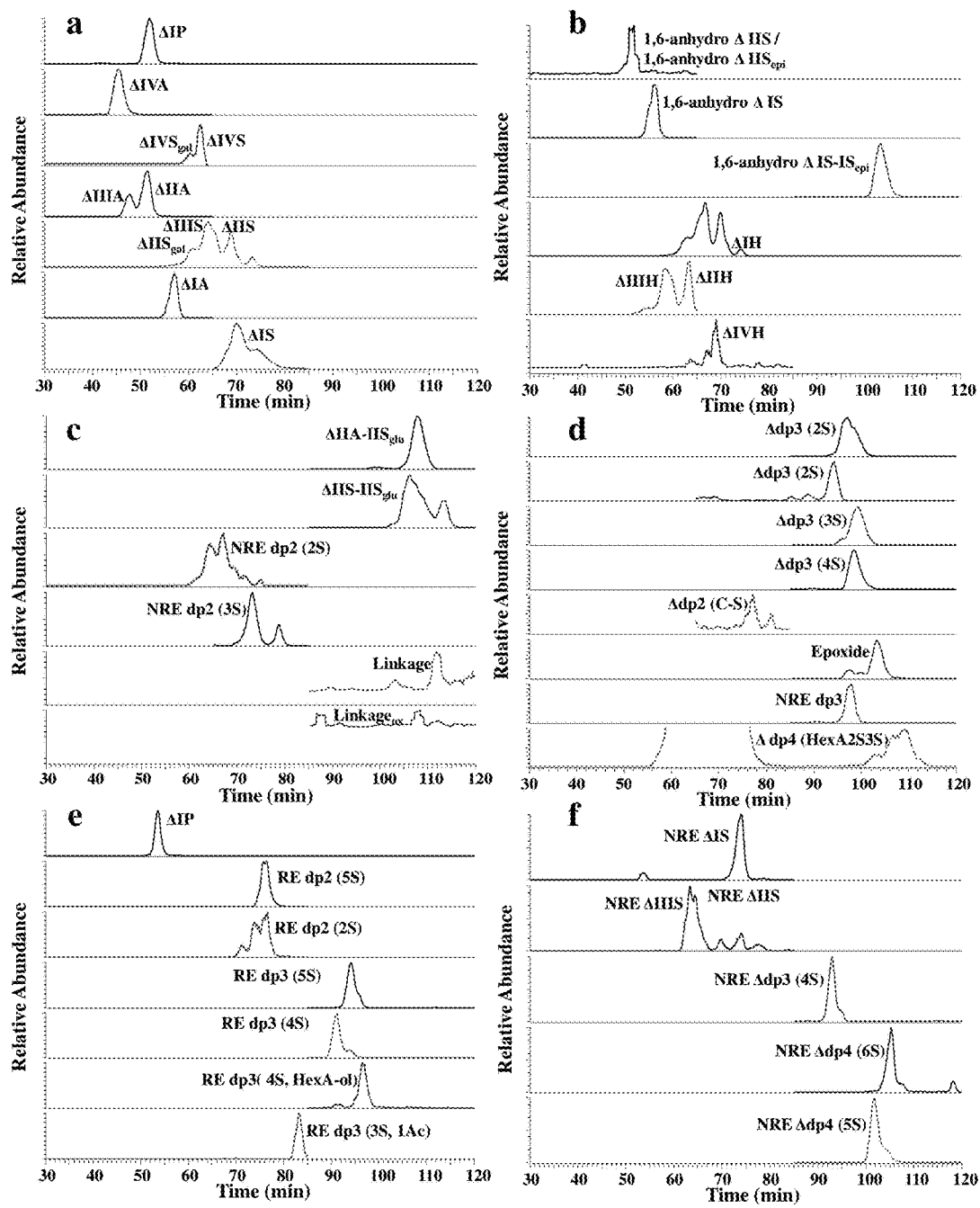

(51) Int. Cl.
*G01N 33/68* (2006.01)
*H01J 49/00* (2006.01)
*H01J 49/42* (2006.01)

(52) U.S. Cl.
CPC ........ *G01N 2400/40* (2013.01); *H01J 49/004* (2013.01); *H01J 49/4215* (2013.01)

DETECTION METHOD FOR LOW MOLECULAR WEIGHT HEPARIN COMPLETE DEGRADATION PRODUCTS USING HYDROPHILIC INTERACTION CHROMATOGRAPHY AND MULTIPLE REACTION MONITORING TANDEM MASS SPECTROMETRY

This application is the U.S. national phase of International Application No. PCT/CN2017/074966 filed on 27 Feb. 2017 which designated the U.S. and claims priority to Chinese Application No. CN2016103301584 filed on 18 May 2016, the entire contents of each of which are hereby incorporated by reference.

TECHNICAL AREA

This invention involves a novel analytical method for complete degradation products of low molecular weight heparin using hydrophilic interaction chromatography tandem multiple reaction monitoring mass spectrometry, which belongs to the technical areas of pharmaceutical, active pharmaceutical ingredients (API) and the detection technic of API.

BACKGROUND TECHNOLOGY

Heparin and its derivatives, low molecular weight heparins (LMWHs) belong to one category of glycosaminoglycan (GAG). They are important anticoagulant drugs resulting from their anticoagulation functions. In order to reduce the risk of side effects, such as bleeding, osteoporosis, thrombocytopenia, and promote the bioavailability, LMWHs are widely utilized as new anticoagulant instead of heparin. LMWHs are manufactured by either enzymatical or chemical degradations making each kind of LMWH possessing its own special structures. Enoxaparin is a LMWH manufactured via alkaline depolymerization of benzyl ester of heparin. Its major non-reducing ends (NREs) are unsaturated uronic acid residues after chemical modification, while saturated uronic acid and amino sugar residues from the parent heparin are also existed. The major reducing ends (RE) are amino sugars which containing 15-25% of 1,6-anhydro structure, also there are a small amount of uronic acid residues and linkage region at the RE. Dalteparin is a kind of LMWH manufactured via nitrous acid degradation. Its major NREs are saturated uronic acid residues, while major REs is mannitol and a small amount of linkage region. In addition to these special ending structures, the backbone also varies during the manufacturing. All above make the analysis of complete degradation products of LMWHs a big challenge. Usually, there are two strategies for heparin analysis, top-down and bottom-up. Bottom-up analysis is the first choice for degradation product analysis. Heparin products generally enzymatically degraded to complete degradation products, and then are analyzed by capillary electrophoresis, high performance liquid chromatography (HPLC) and HPLC tandem mass spectrometry. These conventional methods were mainly focus on the 8 natural disaccharides and only a part of the special structures, not one can perform a comprehensive identification and quantitation analysis on complete degradation products derived from LMWHs. Take enoxaparin for instance, the original ending structures are not able to identified as the newly generated ending structures of building blocks during enzymatic digestion are identical to the original ones. However, these special structures with extremely low content usually contain important structural information related to the quality and safety of drugs. In other words, the characterization of these building blocks are essential.

In addition to the 8 natural disaccharides, the complete degradation products consist of 3-O-sulfated tetrasaccharides which related to the anticoagulation function, trisaccharides generated by peeling reaction, saturated NREs from parent heparin, N-unsubstituted disaccharides and galacturonic acid disaccharides from chemical modification and C-sulfated disaccharide and epoxide structures from molecular rearrangement. Moreover, there are some characteristic structures for different LMWHs, for example, 1,6-anhydro structures in enoxaparin and its original NRE and RE structures, 2,5-anhydro mannitol. No reported methods are able to cover all these building blocks, nevertheless, the analysis of these ending structures and special structures are indispensable for development of LMWH generic drugs, production control and safety control. Moreover, as some of the original ending structures, like enoxaparin, are identical to that of newly generated ending structures after enzymatical digestion, conventional samples preparation strategies are not capable for comprehensive characterization of enoxaparin.

CONTENTS OF THE INVENTION

Aiming at the shortcomings of current analytical techniques for LMWHs, this invention provides a comprehensive identification and quantitation analysis on complete degradation products derived from LMWHs using hydrophilic interaction chromatography (HILIC) tandem multiple reaction monitoring (MRM) mass spectrometry (MS).

This invention is able to distinguish the original NRE and RE structures of LMWH via performing a reduction reaction of the REs of LMWH and degrading the LMWH using hydrogen peroxide. The quantification of all building blocks is achieved by the separation on a HILIC and detected by a MRM tandem MS, especially for the special structures with extremely low relative contents. This new method is applicable to comprehensive characterization of LMWHs.

TECHNICAL PROTOCOLS OF THIS INVENTION

The procedure of this novel analytical method for complete degradation products of low molecular weight heparin using hydrophilic interaction chromatography tandem multiple reaction monitoring mass spectrometry is as follows:

1. Mobile phase A (MPA) is 3 to 10 mM of ammonium acetate in DI water.

2. Mobile phase B (MPB) is 3 to 10 mM of ammonium acetate in 90 to 98% acetonitrile.

3. For the LMWH that needs to distinguish the original ending structures, 10 to 50 μg LMWH sample with internal standard needs to be reduced with sodium borohydride first and hydrolysis using hydrogen peroxide. The dried hydrolysis product is prepared into solutions with the concentration of 1 to 10 μg/μL and go straight to step 4. For those LMWHs do not need to distinguish the original ending structures, 10 to 50 μg dried heparinase digested LMWH sample with internal standard are prepared into solutions with the concentration of 1 to 10 μg/μL for step 4.

4. Solutions prepared in step 3 are centrifuged prior to separation on HILIC column and detection on MRM tandem MS. The flow rate is 0.1 to 0.5 mL/min, and elution gradient are as follows, 0-5 min, 5% MPA, 95% MPB; 5-107 min, 5-23% MPA, 95-77% MPB; 107-112 min, 23-50% MPA, 77-50% MPB; 112-125 min, 50% MPA, 50% MPB;

5. The MRM tandem MS is performed under positive or negative ionization mode on a triple quadrupole MS. The parameters are set as follows, spry voltage under positive ionization mode is +4.0 kV, spry voltage under negative ionization mode is −3.2 kV, the sheath gas flow is 20-30 arb, tube lens voltage is ±50-150 V, collision energy is 20-50.

According to the present invention, heparinase digested LMWH sample with internal standard is dried under vacuum decompression dry for 1 to 3 hours at 30 to 60° C. in step 3.

According to the present invention, the centrifugation condition in step 4 is 10,000 to 15,000 rpm for 5 to 15 min at room temperature. Then further optimized to be 12,000 rpm for 15 min at room temperature.

BENEFICIAL EFFECT OF THIS INVENTION

This invention is capable to comprehensively identify all basic building blocks, not only including the 8 natural heparin disaccharides, but also all reported structures and some new structures. The usage of internal standard helps to relatively quantify all building blocks identified, successfully settled the drawbacks of conventional method. This invention possesses great practical value in LMWH generic drug development, production control and safety control.

FIGURE LEGENDS

FIG. 1. Extracted ion chromatography of enzymatical digested and chemical degraded enoxaparin reference standard in example 1.

Figure 2:
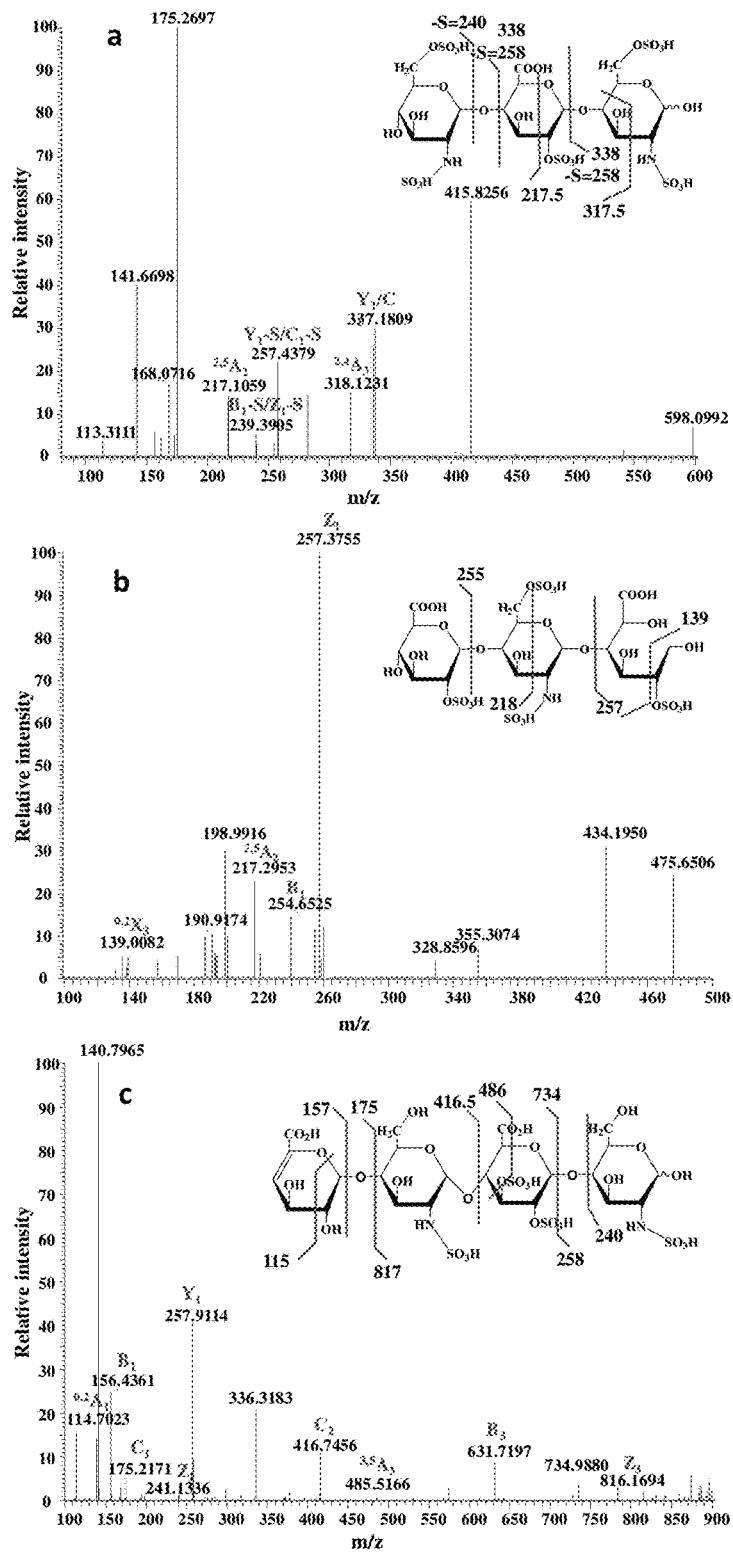

FIG. 2. MS/MS spectra of component 30, 31 of enzymatical digested and RE component 5 of chemical degraded enoxaparin reference standard in example 1. a: MS/MS spectra of component 30 of enzymatical digested enoxaparin reference standard in example 1; b: MS/MS spectra of component 31 of enzymatical digested enoxaparin reference standard in example 1; c: MS/MS spectra of RE component 5 of chemical degraded enoxaparin reference standard in example 1

Figure 3:
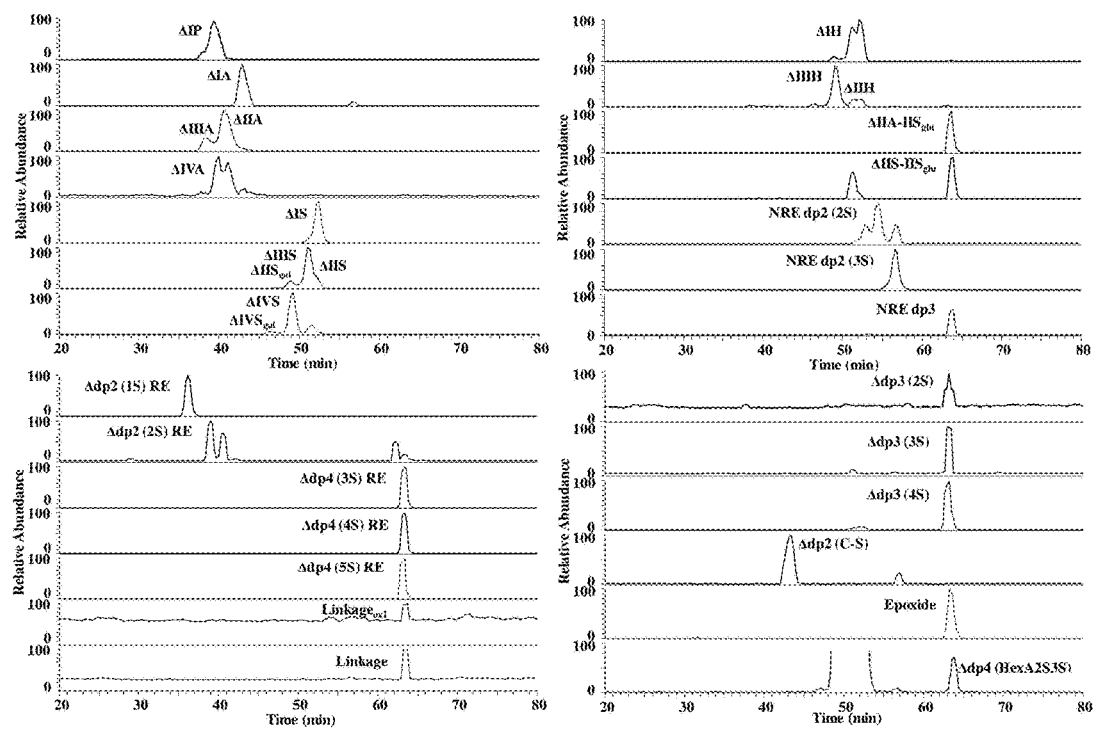

FIG. 3. Extracted ion chromatography of enzymatical digested dalteparin reference standard in example 2

SPECIFIC IMPLEMENTATION METHOD

Further restrictions will be defined by the figures attached combining with the examples below, but not limited as these.

The examples were performed on an Agilent 1100 series HPLC with a ChemStation workstation online coupling to a Thermo TSQ Quantum Ultra triple quadrupole MS with a Xcalibur workstation.

EXAMPLE 1

The procedure of this novel analytical method for complete degradation products of low molecular weight heparin using hydrophilic interaction chromatography tandem multiple reaction monitoring mass spectrometry is as follows:

1. Mobile phase A (MPA) is 5 mM of ammonium acetate in DI water.
2. Mobile phase B (MPB) is 5 mM of ammonium acetate in 95% acetonitrile.
3. Enoxaparin reference standard was enzymatically digested by heparinase I, II and III at 25° C. for 48 h, and internal standard was added before ultrafiltration using a 30 KDa molecular weight cut off membrane. The digests were vacuum decompression dried. The dried digests is prepared into solutions with the concentration of 10 μg/μL and go to step 5.
4. 50 μg enoxaparin sample with internal standard was reducted with sodium borohydride for 12 h first and hydrolysis using hydrogen peroxide. The dried hydrolysis product is prepared into solutions with the concentration of 10 μg/μL and go to step 5.
5. Solutions prepared in step 3 are centrifuged prior to separation on HILIC column with a particle size of 200 Å (2.0 mm×150 mm) and detection on MRM tandem MS. The flow rate is 0.1 to 0.5 mL/min, and elution gradient are as follows, 0-5 min, 5% MPA, 95% MPB; 5-107 min, 5-23% MPA, 95-77% MPB; 107-112 min, 23-50% MPA, 77-50% MPB; 112-125 min, 50% MPA, 50% MPB;
6. The MRM is performed on a Thermo TSQ Quantum Ultra triple quadrupole MS under negative ionization mode on a triple quadrupole MS. The parameters are set as follows, spry voltage under negative ionization mode is −3.2 kV, the sheath gas flow is 20-30 arb, tube lens voltage is ±75 V, collision energy is 35.
7. The concentration (c) of each component can be calculated according to the formula below, $c = c_{IP} \times (A/A_{IP})$, $c_{IP}$ is the concentration of internal standard, A is the area of internal standard and the $A_{IP}$ is the area of this component.
8. The composition analysis of all identified building blocks were performed, the results for building blocks derived via enzymatic digestion are listed in table 1, the results for building blocks derived via chemical degradation are listed in table 2.

TABLE 1

| | Identity | Structure | Theoretical WM | Precursor ions | Charge | Daughter ions |
|---|---|---|---|---|---|---|
| 1 | ΔIS | ΔUA2S-GlcNS6S | 576.9713 | 287.5 | −2 | 138 |
| 2 | ΔIIS | ΔUA-GlcNS6S | 497.0145 | 247.5 | −2 | 138 |
| 3 | ΔIIIS | ΔUA2S-GlcNS | 497.0145 | 247.5 | −2 | 138 |
| 4 | ΔIVS | ΔUA-GlcNS | 417.0577 | 416.0 | −1 | 138, 175 |
| 5 | ΔIA | ΔUA2S-GlcNAc6S | 539.0251 | 268.5 | −2 | 300 |
| 6 | ΔIIA | ΔUA-GlcNAc6S | 459.0683 | 458.0 | −1 | 157, 175 |
| 7 | ΔIIIA | ΔUA2S-GlcNAc | 459.0683 | 458.0 | −1 | 157, 175 |
| 8 | ΔIVA | ΔUA-GlcNAc | 379.1115 | 378.0 | −1 | 115, 175 |
| 9 | 1,6-anhydro ΔIIS | ΔUA-GlcNS-1,6-anhydro | 399.0471 | 398.0 | −1 | 175 |
| | 1,6-anhydro ΔIIS$_{epi}$ | ΔUA-ManNS-1,6-anhydro | | | | |
| 10 | 1,6-anhydro ΔIS | ΔUA2-GlcNS-1,6-anhydro | 479.0040 | 478.0 | −1 | 398 |

TABLE 1-continued

| | Identity | Structure | Theoretical WM | Precursor ions | Charge | Daughter ions |
|---|---|---|---|---|---|---|
| 11 | 1,6-anhydro ΔIS-IS$_{epi}$ | ΔUA2S-GlcNS6S-IdoA2S-ManNS-1,6-anhydro | 1055.9753 | 527.0 | −2 | 406.5 |
| 12 | ΔI-H | ΔUA2S-GlcN6S | 497.0145 | 496.0 | −1 | 258, 416 |
| 13 | ΔII-H | ΔUA2S-GlcN | 417.0577 | 416.0 | −1 | 157, 175 |
| 14 | ΔIII-H | ΔUA-GlcN6S | | | | |
| 15 | ΔIV-H | ΔUA-GlcN | 337.1009 | 336.0 | −1 | 115 |
| 16 | ΔIIA-IIS$_{glu}$ | ΔUA-GlcNAc6S-GlcA-GlcNS3S6S | 1036.0396 | 517.0 | −2 | 175, 458, 616 |
| 17 | ΔIIS-IIS$_{glu}$ | ΔUA-GlcNS6S-GlcA-GlcNS3S6S | 1073.9859 | 536.0 | −2 | 416, 458 |
| 18 | NRE dp2 (2S) | IdoA2S-GlcNS | 515.0251 | 256.5 | −2 | 138, 258 |
| 19 | NRE dp2 (3S) | IdoA2S-GlcNS6S | 594.9819 | 296.5 | −2 | 138 |
| 20 | Linkage | ΔUA-Gal-Gal-Xyl-O-Ser | 719.2120 | 358.6 | −2 | 218, 337 |
| 21 | Linkage$_{ox}$ | ΔUA-Gal-Gal-Xyl-O-Ser$_{ox}$ | 690.1855 | 344.0 | −2 | 189 |
| 22 | Δdp3 (2S) | ΔUA-GlcNS6S-HexA | 673.0466 | 335.5 | −2 | 157, 339 |
| 23 | Δdp3 (2S, 1Ac) | ΔUA-GlcNAc6S-HexA2S | 715.0572 | 356.0 | −2 | 97, 157 |
| 24 | Δdp3 (3S) | ΔUA-GlcNS6S-HexA | 753.0034 | 375.5 | −2 | 193, 314 |
| 25 | Δdp3 (4S) | ΔUA-GlcNS6S-HexA2S | 832.9602 | 415.5 | −2 | 97, 157 |
| 26 | ΔIVS$_{gal}$ | ΔGalA-GlcNS | 417.0577 | 416.0 | −1 | 138, 175 |
| 27 | ΔIIS$_{gal}$ | ΔGalA-GlcNS6S | 497.0145 | 247.5 | −2 | 138 |
| 28 | Δdp2 (C—S) | ΔUA2CS-GlcNS6S | 560.9764 | 279.5 | −2 | 138 |
| 29 | Epoxide | ΔUA2S-GlcNS6S-GlcA-2,3-anhydro-GlcNS | 976.0185 | 478.0 | −2 | 258 |
| 30 | NRE dp3 | GlcNS6S-HexA2S-GlcNS6S | 915.9643 | 457.0 | −2 | 240, 258 |
| 31 | Δdp4 (HexA2S3S) | ΔUA-GlcNS-HexA2S3S-GlcNS | 994.0290 | 496.0 | −2 | 258, 416 |

TABLE 2

| | Identity | Structure | Theoretical WM | Precursor ions | Charge | Daughter ions |
|---|---|---|---|---|---|---|
| | | NREs | | | | |
| 1 | NRE ΔIS | ΔUA2S-GlcNS6S | 576.9713 | 287.5 | −2 | 138 |
| 2 | NRE ΔIIS | ΔUA-GlcNS6S | 497.0145 | 247.5 | −2 | 138 |
| 3 | NRE ΔIIIS | ΔUA2S-GlcNS | | | −2 | |
| 4 | NRE dp3 (4S) | ΔUA-GlcNS6S-HexA2S | 832.9602 | 415.5 | −2 | 157, 193, 273 |
| 5 | NRE dp4 (6S) | ΔUA-GlcNS6S-HexA2S-GlcNS6S | 1153.9427 | 576.0 | −2 | 415.5 |
| 6 | NRE dp4 (5S) | ΔUA-GlcNS6S-HexA2S-GlcNS | 1073.9859 | 536.0 | −2 | 415.5, 375.5 |
| | | REs | | | | |
| 1 | RE dp2 (3S) | HexA2S-GlcNS6S-ol | 596.9976 | 297.5 | −2 | 242, 260 |
| 2 | RE dp2 (2S) | HexA-GlcNS6S-ol HexA2S-GlcNS-ol | 517.0407 | 257.5 | −2 | 242 |
| 3 | RE dp3 (5S) | GlcNS6S-HexA2S-GlcNS6S-ol | 917.9800 | 458.0 | −2 | 242, 260 |
| 4 | RE dp3 (4S) | GlcNS-HexA2S-GlcNS6S-ol | 838.0232 | 418.0 | −2 | 260 |
| 5 | RE dp3 (4S, HexA-ol) | HexA2S-GlcNS6S-HexA2S-ol | 852.9865 | 425.5 | −2 | 257 |
| 6 | RE dp3 (3S, 1Ac) | GlcNAc6S-HexA2S-GlclNS-ol | 800.0769 | 399.0 | −2 | 260 |

Note:
ΔUA represents unsaturated uronic acid, Hex represents uronic acid, GlcA represents glucuronic acid, IdoA represents iduronic acid, GlcN represents glucosamine, Ac represents acetyl group, S represents sulfo group, -ol represents alditol.

The extracted ion chromatography of building blocks derived via enzymatic digestion are shown in FIG. 1, The extracted ion chromatography of building blocks derived via chemical degradation are shown in FIG. 2. This method successfully identified and quantified all possible complete degradation products in enoxaparin.

EXAMPLE 2

The procedure of this novel analytical method for complete degradation products of low molecular weight heparin using hydrophilic interaction chromatography tandem multiple reaction monitoring mass spectrometry is as follows:

1. Mobile phase A (MPA) is 5 mM of ammonium acetate in DI water.
2. Mobile phase B (MPB) is 5 mM of ammonium acetate in 95% acetonitrile.
3. Dalteparin reference standard was enzymatically digested by heparinase I, II and III at 25° C. for 48 h, and internal standard was added before ultrafiltration using a 30 KDa molecular weight cut off membrane. The digests were vacuum decompression dried.
4. The dried digests is prepared into solutions with the concentration of 10 μg/μL and go to step 5.
5. Solutions prepared in step 3 are centrifuged prior to separation on HILIC column with a particle size of 200 Å (2.0 mm×150 mm) and detection on MRM tandem MS. The flow rate is 0.1 to 0.5 mL/min, and elution gradient are as follows, 0-5 min, 5% MPA, 95% MPB; 5-107 min, 5-23% MPA, 95-77% MPB; 107-112 min, 23-50% MPA, 77-50% MPB; 112-125 min, 50% MPA, 50% MPB;
6. The MRM is performed on a Thermo TSQ Quantum Ultra triple quadrupole MS under negative ionization mode on a triple quadrupole MS. The parameters are set as follows, spry voltage under negative ionization mode is −3.2 kV, the sheath gas flow is 20-30 arb, tube lens voltage is ±75 V, collision energy is 35.
7. The concentration (c) of each component can be calculated according to the formula below, $c=c_{IP}\times(A/A_{IP})$, $c_{IP}$ is the concentration of internal standard, A is the area of internal standard and the $A_{IP}$ is the area of this component.
8. The composition analysis of all identified building blocks were performed, the results for building blocks derived via enzymatic digestion are listed in table 3.

TABLE 3

| | Identity | Structure | Theoretical WM | Precursor ions | Charge | Daughter ions |
|---|---|---|---|---|---|---|
| 1 | ΔIS | ΔUA2S-GlcNS6S | 576.9713 | 287.5 | −2 | 138 |
| 2 | ΔIIS | ΔUA-GlcNS6S | 497.0145 | 247.5 | −2 | 138 |
| 3 | ΔIIIS | ΔUA2S-GlcNS | 497.0145 | 247.5 | −2 | 138 |
| 4 | ΔIVS | ΔUA-GlcNS | 417.0577 | 416.0 | −1 | 138, 175 |
| 5 | ΔIA | ΔUA2S-GlcNAc6S | 539.0251 | 268.5 | −2 | 300 |
| 6 | ΔIIA | ΔUA-GlcNAc6S | 459.0683 | 458.0 | −1 | 157, 175 |
| 7 | ΔIIIA | ΔUA2S-GlcNAc | 459.0683 | 458.0 | −1 | 157, 175 |
| 8 | ΔIVA | ΔUA-GlcNAc | 379.1115 | 378.0 | −1 | 115, 175 |
| 9 | Δdp2 (1S) RE | ΔUA-Mnt6S | 402.0468 | 401 | −1 | 243, 285 |
| 10 | Δdp2 (2S) RE | ΔUA2S-Mnt6S | 482.0036 | 481 | −1 | 243 |
| 11 | Δdp4 (3S) RE | ΔUA2S-GlcNS-UA-Mnt6S | 899.0613 | 448.5 | −2 | 243, 255, 339 |
| 12 | Δdp4 (4S) RE | ΔUA2S-GlcNS-UA2S-Mnt6S | 979.0182 | 488.5 | −2 | 243, 339 |
| 13 | Δdp4 (5S) RE | ΔUA2S-GlcNS6S-UA2S-Mnt6S | 1058.9750 | 528.5 | −2 | 157, 409 |
| 14 | ΔI-H | ΔUA2S-GlcN6S | 497.0145 | 496.0 | −1 | 258, 416 |
| 15 | ΔII-H | ΔUA2S-GlcN | 417.0577 | 416.0 | −1 | 157, 175 |
| 16 | ΔIII-H | ΔUA-GlcN6S | 417.0577 | 416.0 | −1 | 157, 175 |
| 17 | ΔIIA-IIS$_{glu}$ | ΔUA-GlcNAc6S-GlcA-GlcNS3S6S | 1036.0396 | 517.0 | −2 | 175, 458, 616 |
| 18 | ΔIIS-IIS$_{glu}$ | ΔUA-GlcNS6S-GlcA-GlcNS3S6S | 1073.9859 | 536.0 | −2 | 416, 458 |
| 19 | NRE dp2 (2S) | IdoA2S-GlcNS | 515.0251 | 256.5 | −2 | 138, 258 |
| 20 | NRE dp2 (3S) | IdoA2S-GlcNS6S | 594.9819 | 296.5 | −2 | 138 |
| 21 | Linkage | ΔUA-Gal-Gal-Xyl-O-Ser | 719.2120 | 358.6 | −2 | 218, 337 |
| 22 | Linkage$_{ox}$ | ΔUA-Gal-Gal-Xyl-O-Ser$_{ox}$ | 690.1855 | 344.0 | −2 | 189 |
| 23 | Δdp3 (2S) | ΔUA-GlcNS6S-HexA | 673.0466 | 335.5 | −2 | 157, 339 |
| 24 | Δdp3 (3S) | ΔUA2S-GlcNS6S-HexA | 753.0034 | 375.5 | −2 | 193, 314 |
| 25 | Δdp3 (4S) | ΔUA2S-GlcNS6S-HexA2S | 832.9602 | 415.5 | −2 | 97, 157 |
| 26 | ΔIVS$_{gal}$ | ΔGalA-GlcNS | 417.0577 | 416.0 | −1 | 138, 175 |
| 27 | ΔIIS$_{gal}$ | ΔGalA-GlcNS6S | 497.0145 | 247.5 | −2 | 138 |
| 28 | Δdp2 (C—S) | ΔUA2CS-GlcNS6S | 560.9764 | 279.5 | −2 | 138 |
| 29 | Epoxide | ΔUA2S-GlcNS6S-GlcA-2,3-anhydro-GlcNS | 976.0185 | 478.0 | −2 | 258 |
| 30 | NRE dp3 | GlcNS6S-HexA2S-GlcNS6S | 915.9643 | 457.0 | −2 | 240, 258 |
| 31 | Δdp4 (HexA2S3S) | ΔUA-GlcNS-HexA2S3S-GlcNS | 994.0290 | 496.0 | −2 | 258, 416 |

Note:
ΔUA represents unsaturated uronic acid, Hex represents uronic acid, GlcA represents glucuronic acid, IdoA represents iduronic acid, GlcN represents glucosamine, Ac represents acetyl group, S represents sulfo group, -ol represents alditol.

The extracted ion chromatography of building blocks derived via enzymatic digestion are shown in FIG. 3. This method successfully identified and quantified all possible complete degradation products in dalteparin.

What is claimed is:

1. A method for testing completely degraded products from low-molecular-weight heparins using a hydrophilic interaction chromatography combined a multiple reaction monitoring mass spectrometry, comprising:
   (1) dissolving ammonium acetate in deionized water up to 3 to 10 mM as mobile phase A (MPA);
   (2) dissolving ammonium acetate in deionized water and adding acetonitrile resulted in mobile phase B (MPB) wherein concentration of ammonium acetate is between 3 and 10 mM and acetonitrile is 90 to 98% by volume;
   (3) reducing 10 to 50 μg of hydrolyzate products, which contains internal standard, of the low-molecular-weight heparins by sodium borohydride for 10 to 12 hours, and hydrolyzing by hydrogen peroxide, then preparing the degraded products from the low-molecular-weight heparins at the concentration between 1 and 10 μg/μL as a test solution for step (4), if end structures of the low-molecular-weight heparins are desired for further identification;
   or preparing the hydrolyzate products, which contains the internal standard, at the concentration between 1 and 10 μg/μL as the test solution for step (4) if the end structures of the low-molecular-weight heparins are not desired for further identification;
   (4) centrifuging the test solution obtained from step (3), loading the supernatant onto a hydrophilic interaction chromatography column for separation: wherein the flow rate is 0.1 to 0.5 mL/min, and elution gradient are as follows: 0-5 min, 5% MPA, 95% MPB; 5-107 min, 5-23% MPA, 95-77% MPB; 107-112 min, 23-50% MPA, 77-50% MPB; 112-125 min, 50% MPA, 50% MPB;
   (5) the multiple reaction monitoring mass spectrometry is performed under positive or negative ionization mode on a triple quadrupole mass spectrometry: wherein the parameters are set as follows, spry voltage under positive ionization mode is +4.0 kV, spry voltage under negative ionization mode is −3.2 kV, the sheath gas flow is 20-30 arb, tube lens voltage is ±50-150 V, collision energy is 20-50.

2. The method according to claim 1, wherein the hydrolyzate products with the internal standard of the low-molecular-weight heparins in step (3) are dried under vacuum decompression dry for 1 to 3 hours at 30 to 60° C.

3. The method according to claim 1, wherein the centrifugation condition in step (4) is 10,000 to 15,000 rpm for 5 to 15 min at room temperature.

4. The method according to claim 3, wherein the centrifugation condition in step (4) is 12,000 rpm for 15 min at room temperature.

* * * * *